United States Patent [19]
Riitano

[11] Patent Number: 5,967,778
[45] Date of Patent: Oct. 19, 1999

[54] APPARATUS AND METHOD FOR DISINFECTING ENDODONTIC INSTRUMENTS DURING USE AND STORAGE

[75] Inventor: Francesco Riitano, Soverato, Italy

[73] Assignee: Ultradent Products, Inc., South Jordan, Utah

[21] Appl. No.: 09/014,765

[22] Filed: Jan. 28, 1998

[51] Int. Cl.[6] .................................................. A61G 15/00
[52] U.S. Cl. ............................ 433/77; 433/102; 206/366
[58] Field of Search ..................... 433/77, 102; 206/366, 206/368, 369

[56] References Cited

U.S. PATENT DOCUMENTS

| | | | |
|---|---|---|---|
| 2,210,318 | 8/1940 | Eckert | 206/368 |
| 3,248,167 | 4/1966 | Friedman | 433/25 |
| 3,911,587 | 10/1975 | Forrest et al. | 33/174 |
| 4,028,810 | 6/1977 | Vice | 433/102 |
| 4,165,562 | 8/1979 | Sarfatti | 433/102 |
| 4,212,639 | 7/1980 | Schaffner | 433/72 |
| 4,232,784 | 11/1980 | Hesselgren | 433/77 |
| 4,353,694 | 10/1982 | Pelerin | 433/102 |
| 4,382,788 | 5/1983 | Pelerin | 433/77 |
| 4,503,972 | 3/1985 | Nelligan et al. | 206/369 |
| 4,936,449 | 6/1990 | Conard et al. | 206/366 |
| 4,976,615 | 12/1990 | Kravitz | 433/102 |
| 5,743,734 | 4/1998 | Heath et al. | 433/77 |

Primary Examiner—John J. Wilson
Attorney, Agent, or Firm—Workman, Nydegger, Seeley

[57] ABSTRACT

A dental or medical instrument containing device includes a container and a supporting material. The supporting material supports an instrument, such as an endodontic file, within the container. A disinfecting solution within the container permeates the supporting material such that a distal insertion end of the instrument is immersed within the disinfecting solution. The disinfecting solution is preferably capable of maintaining the distal insertion end of the instrument in at least an aseptic condition. The supporting material maintains the instrument in an upright position such that the proximal end of the instrument is readily grasped.

20 Claims, 4 Drawing Sheets

APPARATUS AND METHOD FOR DISINFECTING ENDODONTIC INSTRUMENTS DURING USE AND STORAGE

BACKGROUND OF THE INVENTION

1. The Field of the Invention

This invention is useful in the dental and medical arts. The invention relates to a container configured to maintain a portion of a dental or medical instrument in at least an aseptic condition. Additionally, the invention enables instruments to be easily grasped with a mechanical handpiece and to then be repositioned within a supporting material.

2. The Relevant Technology

When engaging in dental procedures, it is important that the dental instruments employed do not introduce infection into the mouth of the patient. Avoiding the introduction of microorganisms to the area of a tooth being treated is particularly important when performing root canal therapy since infections cause significant problems in root canals. In fact, the inability to successfully counteract harmful microorganisms in a root canal is the primary reason that infected or potentially infected tissue is removed from a root canal during endodontic or root canal therapy. Accordingly, it is important to avoid introducing any additional microorganisms into the root canal.

As part of the root canal therapy, the practitioner typically employs endodontic files to file the root canal and remove infected material. Endodontic files typically comprise a thin, distal insertion end and a proximal gripping end held by a practitioner or inserted into mechanical instruments such as a drill. The thin distal insertion end is often a delicate, flexible tip with sharp edges to enable efficient cleaning of the root canal.

To reduce the possibility of causing infection while working within a dental patient's mouth, it is vital that endodontic files and other dental instruments be maintained in a disinfected environment before and during use. In light of this need for a sterile technique, a variety of different disinfecting dental instrument containers have been developed.

For example, certain dental instrument containers have been produced which are capable of being placed in an autoclave, thereby sterilizing the instruments in the container. Other dental instrument containers have been developed which contain a disinfecting solution for placement of dental instruments into the solution. U.S. Pat. No. 3,248,167 to Friedman, for example, discloses a magnetic dental burr holder. The magnetic burr holder features a box-like container which contains a sterilizing solution. The container includes a hinged lid having a magnetized inner surface. Dental burrs are demountably coupled to the magnetized inner surface such that when the lid is closed, the tips of the dental burrs are immersed in the sterilizing solution.

However, magnetized containers may only be employed to maintain certain metal instruments within a solution. The magnetic container could not be employed to maintain a plastic instrument or the plastic portion of an instrument in a desired position. Endodontic files, for example, often include a non-metallic (e.g. plastic) proximal gripping end. Furthermore, containers made from some metals can be corroded through contact with certain liquids. Additionally, use of metal containers can also be disadvantageous due to their relative weight and due to their cost, which may prevent their use on a disposable basis.

Other containers include a well or reservoir for containing both a sterilizing solution and an instrument immersed in the solution, such as the container disclosed in U.S. Pat. No. 4,306,862. However, a mere reservoir fails to maintain a portion of the dental instrument outside of the reservoir. Thus, when a practitioner desires to grasp the dental instrument, the practitioner must immerse the practitioner's fingers or another dental instrument into the sanitary solution, potentially permitting infectious material to pollute the solution.

U.S. Pat. No. 4,232,784 to Hesselgren discloses a stand for instruments for medical use. This stand features sheets of paper arranged vertically close together. The sheets are held close together by the stand. Dental instruments are inserted between the sheets for storage during a sterilization process. To protect the dental instruments from corrosion during a sterilization process, the sheets are impregnated with a corrosion inhibitor. The sterilization process involves either autoclave sterilization in saturated water vapor at 120° C. to 130° C. or by means of dry sterilization at 180° C.

One of the problems associated with a paper stand as disclosed in U.S. Pat. No. 4,232,784 is that the instrument must be placed between the paper sheets. The practitioner must therefore take time to ensure that the instrument is not directed into the paper which may potentially bend the instrument. The corrosion inhibitor may cause the papers to clump together, thereby losing their ability to receive a dental instrument. Furthermore, if papers on one side clump together, the papers on an opposing side could be separated too broadly, such that the dental instruments would slip between the cracks, precluding convenient gripping of the gripping end. The paper could also flake off onto the tips when wet or when ripped from the container. Additionally, as stated at column 3, lines 3–6 after having been used a number of times the instrument stand is considered expended. The stand cannot be used to maintain an instrument in a desired position after a few insertions of instruments as the instruments either break or weaken the fiber matrix of the paper or due to the debilitating impact of either the corrosion inhibitor or sterilization process on the paper.

As an additional difficulty within the art, typical dental instrument containers are complex and expensive structures containing a variety of reservoirs, ports and apertures for the placement of solution and instruments. The formation of these reservoirs, for example, for holding particular instruments therein, requires molding and extrusion processes which are expensive and complex. In addition, in use, the dental instrument must be placed in a specific hole or in a hole selected from a specific series of holes.

Another problem within the art is that sterilizing containers typically do not allow a practitioner to remove debris from the instruments placed within the containers. Instead, relatively large pieces of debris may remain disposed on the instrument while the instrument is placed in a sterilizing solution, hampering the sterilization process.

Based on the foregoing, there is a substantial need within the art for a container which is configured to maintain a dental instrument in at least an aseptic condition. There is also a substantial need for such a container which features efficient cleaning of a dental instrument within the container. Additionally, there is also a substantial need for a container which can be repeatedly used to enable an instrument to be positioned at various locations in the container without damaging the instruments, to be supported in an upright position and to then be easily grasped by hand or by a mechanical handpiece. There is also a substantial need for a container which enables a practitioner to remove debris from a dental instrument and to minimize the potential for cross-contamination between instruments. Further, there is also a need in the art to provide an improved container which is inexpensive, efficient to manufacture, and is disposable. Finally, there is also a substantial need for a kit, and methods of use and manufacture relating to such a container.

SUMMARY AND OBJECTS OF THE INVENTION

It is therefore an object of the invention to provide an improved container for dental and medical instruments, and a kit and methods of use and manufacture relating to an improved instrument container.

Another object of the invention is to provide a container which is configured to maintain a dental or medical instrument in at least an aseptic condition.

An additional object of the invention is to provide a container for dental or medical instruments which enables the instruments to be efficiently cleaned.

It is another object of the invention to provide a container which can be repeatedly to used to enable an instrument to be randomly positioned within a supporting material without damaging the instruments, to be supported in an upright position and to then be easily grasped by hand or by a mechanical handpiece.

Yet another object of the invention is provide a containing device which can remove debris from dental or medical instruments and also minimizes the potential for cross-contamination between instruments.

Finally, it is an object of the invention is to provide an efficient, light-weight, portable, inexpensive, disposable container for dental or medical instruments which is simple in design and does not necessarily require the expensive extrusion of specific shapes including holes and other complex designs for maintaining the dental or medical instruments within the container.

The container can be used with medical instruments including dental instruments. Although, reference is primarily made specifically to dental instruments, the container can be used with other instruments as well so the term "dental instrument" is interchangeably used with the term "medical instrument" or "instrument".

An instrument containing device of the present invention includes a container and a supporting material which is configured to support a dental or medical instrument, such as an endodontic file, within the container. A disinfecting solution is disposed within the container such that at least a portion of the distal insertion end of the instrument is immersed within the disinfecting solution, thereby disinfecting the immersed portion. In one embodiment, the disinfecting solution permeates the supporting material. The disinfecting solution is preferably capable of maintaining the distal insertion end of the instrument in at least an aseptic condition.

The container is configured to be hand held and the supporting material is configured such that a practioner can hold a handpiece in the other hand and easily remove an instrument from the supporting material with the handpiece. More specifically, the supporting material is configured to maintain the instrument in an essentially upright position such that a proximal gripping end of the instrument can be readily grasped by a user or practioner with a handpiece or other mechanical instrument. The supporting material is also configured such that the instrument can be reinserted back into the supporting material while being held by the mechanical instrument and then be released in an essentially upright position. Accordingly, it is unnecessary for a user to touch the instrument which minimizes contamination of the instrument. Avoiding touching of the instrument is particularly important when the instrument is utilized during a procedure, such as root canal therapy.

To avoid any touching through the use of the handpiece, the supporting material must have particular properties such that the instrument can be supported, the instrument can be released, the instrument can be reinserted and then held in place as the instrument is disconnected from the handpiece. For example, the supporting material may be required to grip the instrument to some extent during disconnection of the handpiece from the instrument such that instrument remains in position. The supporting material also has properties which enable repeated use such that an instrument can be repeatedly removed from the supporting material and reinserted into the supporting material in a manner such that the instrument is maintained in an essentially upright position after reinsertion.

The instrument and the containing device collectively form an instrument kit, such as a disposable endodontic file kit. In light of the arrangement of the kit, the practitioner can grip the proximal end of the instrument and readily remove the instrument from the container without interfering with other instruments and without contaminating the solution or the distal end of the instrument. Because the container contains a supporting material that is generally lightweight, the container is lightweight, portable and inexpensive to produce.

Also because of the configuration and properties of the supporting material, the container supports instruments in the desired position without necessarily requiring the molding or the extrusion of recesses, reservoirs, or other shapes specifically designed to hold certain instruments. Instead, the instruments can be placed anywhere within the supporting material rather than being required to be placed in certain predetermined areas. Accordingly, the disposable container is efficient to make and use.

The supporting material is also sufficiently penetratable or deformable that it will not bend, blunt or otherwise damage instruments placed within the supporting material. Because of the configuration and properties of the supporting material, it is possible to place any instrument, including metallic, non-metallic and partially metallic instruments, into the supporting material and preferably in contact with the disinfecting solution. The supporting material can also remove debris without damaging the instruments when an instrument is placed into or removed from the supporting material. Methods of manufacture and use are also disclosed.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
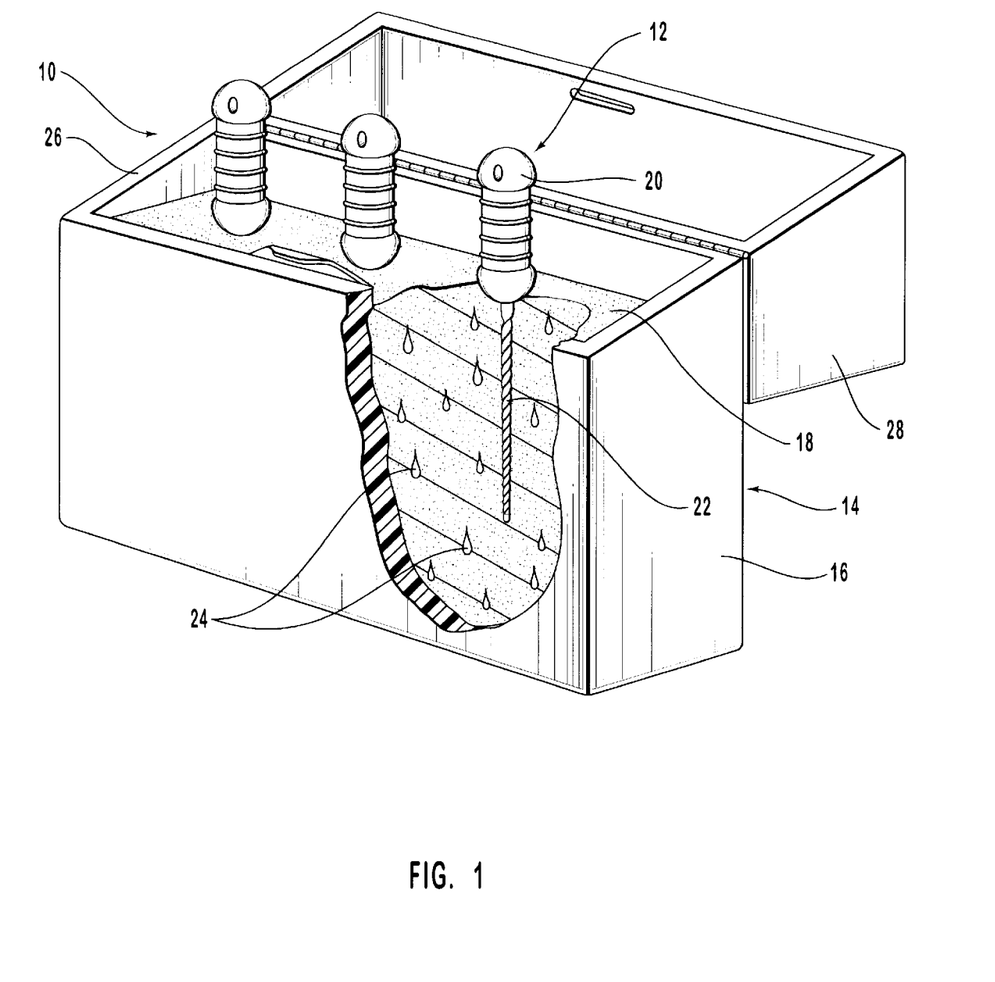
FIG. 1 demonstrates a perspective view of a dental instrument kit of the present invention comprising an instrument containing device and a dental instrument. A portion of the container is cut away.

FIG. 1 demonstrates an instrument kit 10 of the present invention comprising a dental instrument 12 and an instrument containing device 14. Dental instrument 12 has a proximal gripping end 20 or handle opposite a distal insertion end 22 or file.

As shown in FIG. 1, instrument containing device 14, comprises (i) a container 16 which is adapted to be hand held; (ii) a supporting material 18 disposed within container 16 and configured to support dental instrument 12 within container 16; and (iii) a disinfecting solution 24 disposed within container 16 and permeating supporting material such that distal insertion end 22 of dental instrument 12 can be immersed within disinfecting solution 24, thereby disinfecting distal end 22.

During storage, distal insertion end 22 of dental instrument 12 is inserted within solution permeated material, thereby disinfecting insertion end 22 and protecting insertion end 22 against outside contamination. Supporting material 18 is configured to maintain an instrument 12 in an essentially upright position, such that proximal gripping end 20 can be readily grasped. During a procedure, such as a dental procedure, proximal end 20 can be either grasped by the user or connected to a mechanical instrument, such as a handpiece operated by the user while the user holds container 16 with the opposite hand.

It is preferable to grasp proximal end 20 of instrument 12 with a handpiece and then after use of the instrument 12 to reinsert instrument 12 into supporting material 18 and release the handpiece from instrument 12 instead of manually grasping instrument 12. It is preferable to use a handpiece in combination with instrument kit 10 to avoid any touching by a user or practioner. While only three instruments 12 are depicted in FIGS. 1–4, any number of instruments may be positioned within material 18. For example, when utilized in some endodontic procedures about twenty-four instruments 12 may be positioned in material 18 such that the entire endodontic procedure may be completed without any contamination due to human contact with the instruments 12.

Additionally, in light of the arrangement of dental kit 10, the practitioner can grip proximal end 20 of instrument 12 and readily remove instrument 12 from containing device 14 without interfering with other instruments and without infecting disinfecting solution 24. Dental instrument 12 of FIG. 1 comprises an endodontic file; however, dental instrument 12 can be any dental instrument or medical instrument that requires cleaning of one end that is opposite a gripping end.

Containing device 14 will now be described in additional detail with continued reference to FIG. 1. Container 16 of device 14 is intended to be inexpensive, lightweight, disposable, and portable. Accordingly, the container is preferably formed from plastic. Container 16, may, however, be comprised of any suitable material, such as metal or a ceramic material. Container 16 may also be configured in a variety of shapes, any of which are suitable for maintaining a disinfecting solution 24 and a supporting material 18 therein.

As shown in FIG. 1, container 16 has an open end 26. Lid 28 hingeably coupled to container 16 serves as an example of means for sealing open end 26 of container 16, thereby preventing substantial ingress of dust, air, and contaminants into containing device 14.

Supporting material 18 will now be described in additional detail. Supporting material 18 preferably has sufficient porosity or deformability to enable an instrument to be inserted into the supporting material without bending, blunting or otherwise damaging instruments placed within the material cushioning. Supporting material 18 is also preferably sufficiently elastomeric or resilient to allow the material to substantially return to its original configuration before an instrument was inserted after the instrument has been removed such that supporting material 18 is not permanently deformed by insertion of instruments 12 therein. Additionally, supporting material is preferably sufficiently elastomeric or resilient such that an instrument can be repeatedly inserted into approximately the same location and still be retained by the material and held in an essentially upright position. The resiliency of the material also preferably prevents the material from being substantially torn or the matrix of the material from being substantially disrupted due to the brittleness of the material. Accordingly, material 18 preferably enables containing device 14 to be reusable as instruments 12 may be inserted, removed and reinserted many times and still be maintained in an essentially upright position after reinsertion.

A variety of examples of supporting material 18 can be employed in the present invention. Cellular foam materials are particularly useful due primarily to having sufficient porosity for easy insertion of an instrument. Examples of cellular foam materials include a polymeric foam, foam rubber, styrofoam, or any material comprising a light-weight cellular foam. While naturally occurring foam materials, such as a sponge can be utilized, synthetic foam materials are generally preferred. Additionally, other suitable synthetic materials can also be utilized including plastic mesh or strands of intertwined plastic, such as nylon. Intertwined metal strands, such as steel wool, can also be utilized. Less porous materials can also be utilized such as a relatively dense rubber that is still sufficiently deformable and elastomeric to enable an instrument to be inserted into the material.

Supporting material 18 may be of any size, shape or density which enables the supporting material 18 to be disposed within a container 16 and support instruments 12 in the container 16, preferably while instruments 12 are at least partially immersed in solution 24. Supporting material 18 may also be disposed in a variety of locations within container 16 so long as supporting material 18 supports dental instrument 12 and preferably enables solution 24 to disinfect at least a portion of dental instrument 12.

Supporting material 18 is preferably sufficiently porous that insertion end 22 of instrument 12 may be disposed in supporting material 18. Additionally, supporting material 18 is preferably sufficiently porous that solution 24 can permeate supporting material 18. In one embodiment, the diameter of insertion end 22 is roughly the diameter of certain pores or openings of supporting material 18. In another embodiment, the diameter of insertion end 22 is slightly larger than the diameter of the pores such that insertion end 22 slightly and nonpermanently deforms the pores as they are inserted therein.

Supporting material 18 can also be selected to have a structure, such as pore size or length, which permit insertion of only distal insertion end 22 into supporting material 18 while preventing insertion of the proximal end 20 such that distal insertion end 22 rests on supporting material 18. Accordingly, when utilized with an endodontic file instrument such as the instrument shown at 12, which typically has a proximal end with a diameter that is substantially larger than the distal insertion end, such a configuration ensures that the proximal end is easily grasped.

It is also preferred that supporting material 18 be able to retain an instrument against the forces of gravity until it is pulled out of supporting material 18. The ability to retain an instrument can result from the particular configuration of the material or due to the properties of the material such as the porosity, elasticity, resilience or deformability.

Supporting material 18 is also sufficiently rigid that it maintains instrument 12 in an essentially upright position. Additionally, supporting material 18 is sufficiently rigid to enable a practitioner to easily connect a handpiece to proximal gripping end 20 while distal insertion end 22 of instrument 12 is positioned within supporting material 18 and to then reposition distal insertion end 22 into supporting material 18 and disconnect the handpiece from proximal gripping end. The ability of supporting material 18 to grip distal insertion end 22 in order to disconnect the handpiece from instrument 12 may also be related to having varying pore sizes or the degree to which supporting material 18 is intertwined.

Additionally, the properties of supporting material 18 are adequately uniform that supporting material 18 permits insertion of distal insertion end 22 into any portion of supporting material 18 without damaging the distal insertion end. Accordingly, the practitioner is enabled to efficiently dispose the instruments 12 into any desired, random position and need not take the time to ensure that distal insertion end 22 is positioned into a particular preformed orifice, in between compressed sheets or other specific, predesignated location. Thus, containing device 14 supports dental instruments in the desired position without necessarily requiring the molding or extrusion of recesses, reservoirs, or other specific shapes designed to hold certain instruments, as required in previous designs. There is no need for external support, such as trays having recesses or apertures for placement of instruments therein. Due to the uniform properties of supporting material 18 which enables random placement of distal insertion ends 22, containing device 14 is simple, inexpensive, and efficient to produce.

Supporting material 18 also receives and supports instruments having a variety of different shapes and sizes, without preforming a certain reservoir to fit the particular size and shape, such as length or width, of the insertion end or other portion of the instrument. Thus, instruments with long insertion ends, for example, can be placed adjacent instruments with short insertion ends without necessarily requiring a predetermined hole for each instrument.

Supporting material 18 acts as a shock absorber, thereby preventing dental instruments from contacting each other and preventing the bending, blunting or otherwise damaging of the delicate, thin, sharp distal insertion ends of instruments such as dental files during movement of the container. Supporting material 18 also enables a practitioner to maintain metallic, non-metallic and partially metallic dental instruments within disinfecting solution 24.

The structure of supporting material 18 also enables a practitioner to remove debris from instrument 12 without damaging instrument 12 by rubbing instrument 12 against supporting material 18, such as by placing end 22 within supporting material 18 or removing end 22 from supporting material 18. As a significant benefit, debris can be removed and instrument 12 can be simultaneously disinfected without damaging instrument 12 by placing distal insertion end 22 of instrument 12 within supporting material 18 or removing distal insertion end 22 of instrument 12 from supporting material 18.

Figure 3:
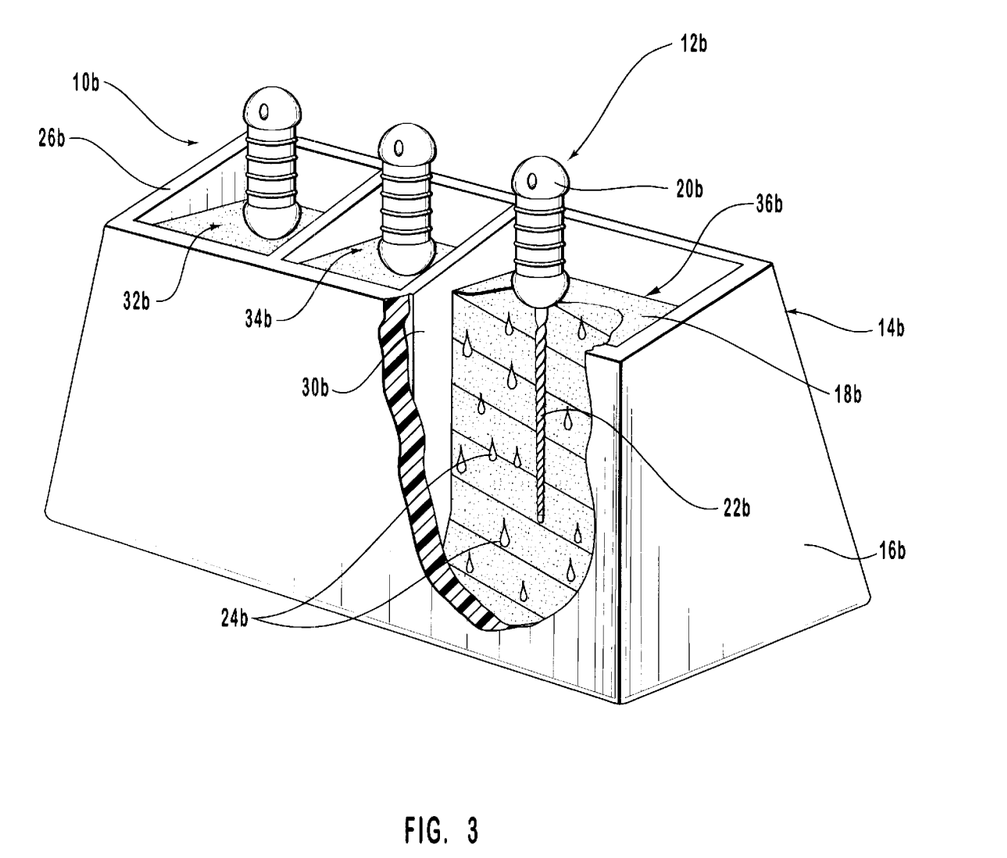
FIG. 3 demonstrates a perspective view of yet another alternative dental kit of the present invention having a compartmentalized interior.

Supporting material 18 may also be retained in a desired position within container 16 through the use of a variety of different means for retaining supporting material 18 in a desired position within container 16, such as an adhesive, one or more lips, a friction fit between densely packed supporting material 18 and container 16, or by configuring container 16 such that the upper end thereof is narrower than the wider end (as shown in FIG. 3 for example), thereby providing a wedged fit for supporting material 18 within container 16 which prevents supporting material 18 from slipping out of container 16. In one embodiment (not shown), a lip inside containing device 14 maintains supporting material 18 snugly within a desired position in container 16 by being placed above supporting material 18 in container 16.

In one embodiment, disinfecting solution 24 comprises at least one antimicrobial agent capable of eliminating or at least preventing the growth of microorganisms. Solution 24 can contain any suitable antimicrobial agent. Specific examples of suitable antimicrobial agents include organochlorides, such as chlorohexidine and cetylpyridinium chloride.

Preferably, solution 24 is capable of maintaining the distal insertion end 22 of the dental instrument in at least an aseptic condition. The phrase "at least an aseptic condition" as used throughout this specification and the appended claims refers to a condition ranging between aseptic and sterile.

Device 14 may contain a variety of different dental instruments, such as dental files, syringe tips, adapters, needles, posts for placement of crowns, etc. However, while it will be appreciated that a variety of different instruments may be stored in containing device 14, endodontic file instruments are particularly benefitted by being stored in containing device 14.

Endodontic procedures are commonly long, awkward procedures which are uncomfortable for the patient. During these procedures, the patient typically remains in the dental chair for an extended period of time and receives a local and/or general anesthetic to ameliorate the pain and discomfort associated with the procedure. During the procedure, the practitioner often employs a series of different file instruments to clean and file a patient's root canal, for example. Endodontic file instruments 12 are necessarily small, delicate instruments. Fumbling for the gripping end 20 of the file instrument 12 increases the time and frustration associated with placing the small, delicate instruments in the enclosed spaces of root canals, for example.

Containing device 14 is particularly useful for containing endodontic files 12 because it simplifies and hastens the endodontic procedure. In addition to disinfecting and removing debris from a particular dental instrument 12, containing device 14 maintains instruments 12 in an essentially upright position, ready for grasping by a practitioner. Since decreased procedure time and simplicity are important, kit 10 is a significant advance within the art of endodontistry and other fields of medicine and dentistry.

The diameter of the insertion ends 22 or file of endodontic file instruments 12 must be small enough to be inserted into a root canal of a tooth while the gripping end 20 is preferably large enough to be grasped by a practitioner or a mechanical instrument. For example, in one embodiment, the diameter of the distal insertion ends 22 of the endodontic files is in a range of about 0.06 mm to about 2 mm; while the diameter of the proximal gripping end 20 of instrument 12 is substantially greater, meaning that the diameter of gripping end 20 is at least about two times greater than the diameter of insertion end 22.

Containing device 14 is useful for containing endodontic files 12 because, at least in one embodiment, the pores of supporting material 18 roughly correspond to the diameter of the insertion ends 22 of the files 12 or are slightly smaller, and are too small to receive the substantially greater diameter of the gripping ends 20 of the files 12, thereby preventing the gripping ends 20 from extending into the supporting material 18. Thus, supporting material 18 permits insertion of distal insertion end 22 into supporting material 18, but prevents insertion of the proximal end 20 of endodontic file 12 into supporting material 18, such that proximal end 20 of file 12 is readily grasped. Accordingly, the practitioner can also know precisely which portion of the instrument has been disinfected.

Moreover, the thin, delicate, sharp insertion ends of endodontic files readily pierce a variety of densities of supporting material 18 during insertion into supporting material 18 and are protected within supporting material 18 without being blunted by supporting material 18. Finally, in the present invention, the insertion ends or files of the endodontic file instruments are preferably soaked in the solution until ready for use (or between uses), and do not introduce infection into the root canal while attempting to disinfect the root canal.

Examples of methods of manufacture and use of containing device 14 and kit 10 will now be discussed. One example of a method for manufacturing device 14, comprises: (i) providing a container 16; (ii) disposing a material within the container which is configured to support a dental instrument within the container 16 and to maintain the dental instrument in an essentially upright position in the container 16; and (iii) placing disinfecting solution 24 within container 16, e.g., by permeating supporting material 18 with disinfecting solution 24, such that distal insertion end 22 of dental instrument 12 is immersed within and disinfected by disinfecting solution 24.

One example of a method for disinfecting a portion of a dental instrument, comprises (i) providing an instrument containing device 14, which includes disinfecting solution 24 and supporting material 18; and (ii) placing end 22 of dental instrument 12 within supporting material 18 in container 16. Instrument 12 can be readily removed from supporting material 18, then replaced in the same or a different location following use in a procedure. Preferably, the dental instrument 12 is placed in supporting material 18 in an essentially upright position such that the proximal end 20 of the dental instrument 12 is readily grasped by a practitioner.

Optionally, after supporting material 18 is disposed in container 16, end 22 is first placed in supporting material 18, after which disinfecting solution 24 is placed in container 16, e.g. by permeating supporting material 18, such that distal insertion end 22 of dental instrument 12 is immersed within disinfecting solution 24. It will thus be appreciated that disinfecting solution 24 may be added at any time before or after use of instrument 12. For example, disinfecting solution 24 may be added before kit 10 is sent to a practitioner. Optionally, disinfecting solution 24 may be poured through supporting material 18 by the practitioner before use.

Figure 2:
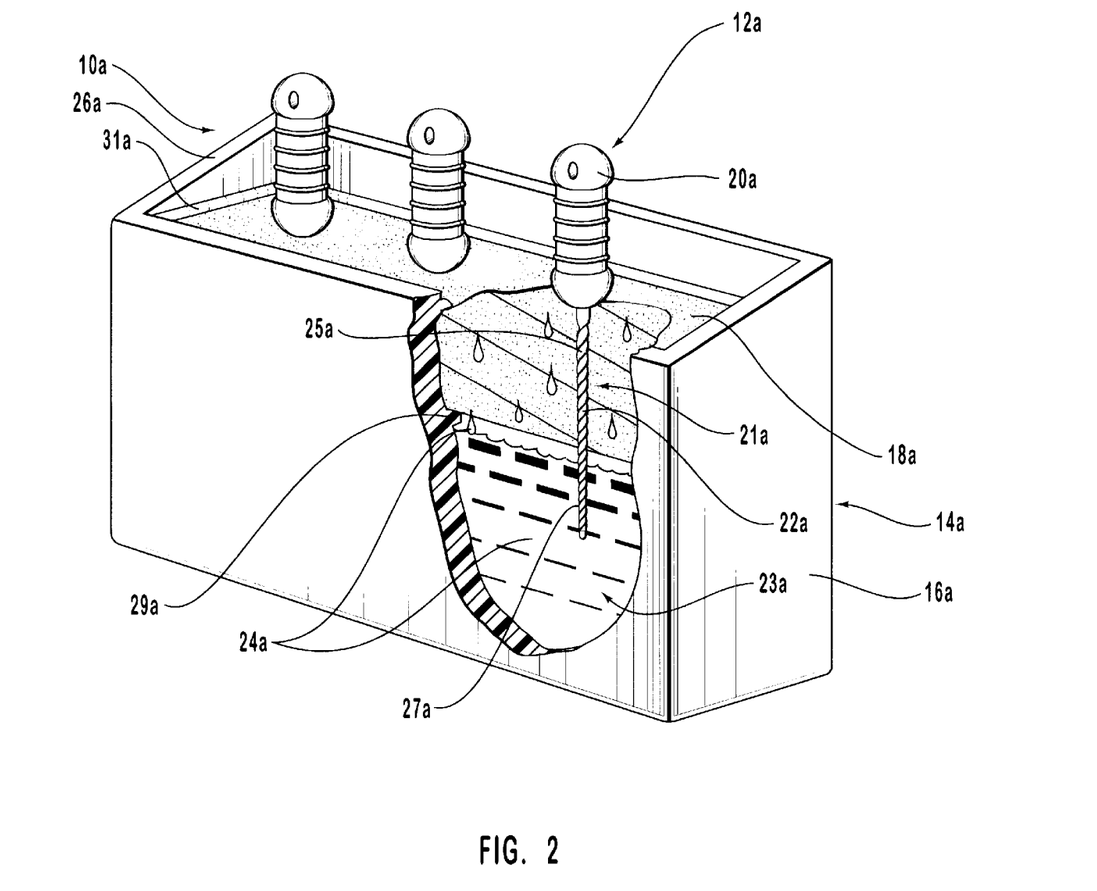
FIG. 2 demonstrates a perspective view of an alternative dental kit of the present invention having an upper portion of solution permeated supporting material and a lower portion of solution only.
Figure 4:
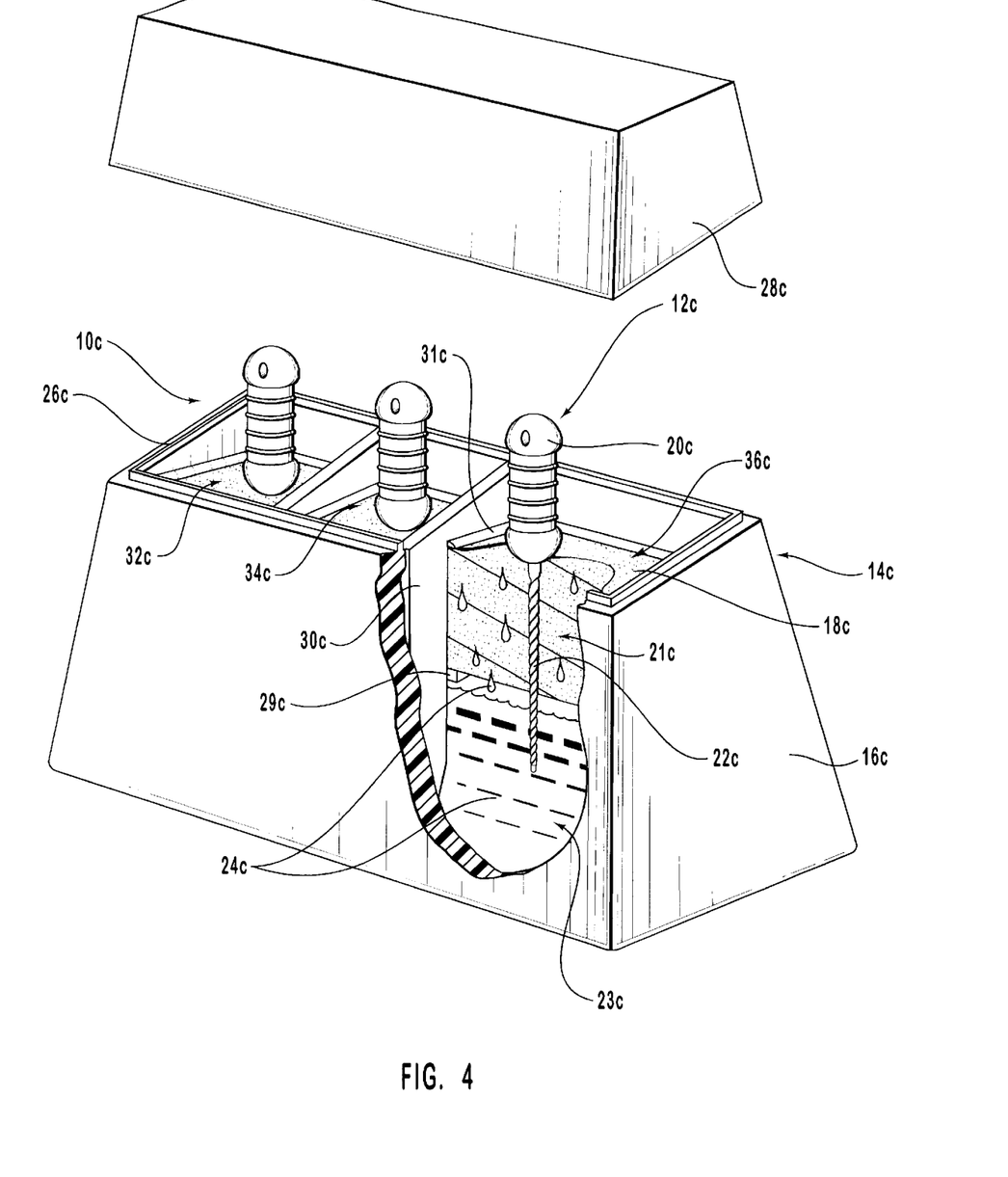
FIG. 4 demonstrates a perspective view of yet another alternative dental kit of the present invention having a compartmentalized interior, each compartment having an upper portion of solution permeated supporting material and a lower portion of solution only.

Alternative embodiments of kits 10a, 10b, and 10c are demonstrated in FIGS. 2, 3, and 4 respectively. As shown in FIG. 2, it is possible to provide (i) an upper portion 21a comprising a supporting material 18a and disinfecting solution 24a; and (ii) a lower portion 23a comprising disinfecting solution 24a only. In this embodiment, instrument 12a is maintained in an essentially upright position by supporting material 18a while distal insertion end 22a of instrument 12a is immersed in and disinfected by solution 24a. This embodiment allows a practitioner to conserve the amount of supporting material 18a employed, while nevertheless accomplishing the goals of the invention. In addition, the lower portion 27a of distal insertion end 22a is in more concentrated contact with solution 24a.

In one embodiment, supporting material 18a is maintained above solution 24a through the use of a lower lip 29a on the interior surface of container 16a, while upper lip 31a prevents supporting material 18a from slipping out of container 26a. Both lips serve as examples of means for retaining supporting material 18a in a desired position within container 16.

As shown in FIGS. 1 and 2, it is possible to accomplish the goals of the invention by placing at least a portion of the distal insertion end of the instrument into the material while at least a portion of the distal insertion end is immersed in and disinfected by the solution. Thus, the entire distal insertion end may be disposed in material and solution (see FIG. 1), or an upper portion thereof may be disposed in material (and solution if desired) while a lower portion is disposed in solution only.

As one example, as shown in FIG. 2, only an upper portion 25a of distal insertion end 22a is disposed in supporting material 18a (which supports instrument 12a in an upright position), while a lower portion 27a of distal insertion end 22a is disposed in solution 24a only. Nevertheless, both upper and lower portions 25a, 27a of distal insertion end 22a are immersed in and disinfected by solution 24a.

As another example, in another embodiment (not shown), the upper portion of the containing device comprises material only while the lower portion comprises disinfecting solution only. In this embodiment, the upper portion of the distal insertion end is disposed in the upper material portion, which supports the instrument in an upright position. Only the lower portion of the distal insertion end is disposed in and disinfected by the solution.

As shown in FIG. 3, in another embodiment, a series of internal dividers 30b form separate compartments 32b, 34b, 36b within container 16b, thereby allowing a practitioner to maintain different solutions within container 16b or preventing the mixing of fresh disinfecting solution in one compartment with solution in another compartment which contains a number of used instruments. Each compartment 32b, 34b, 36b contains a separate piece of supporting material 18b.

As another advantage of the compartments, it is possible to remove debris from instrument 12b in one compartment while preserving the other compartments for use before or after the removal of debris. This prevents debris from entering the preserved compartments, yet still enables a practitioner to simultaneously remove debris and disinfect instrument 12b by placing instrument 12b into container 16b or removing instrument 12b from container 16b.

As shown in FIG. 3, in one embodiment, the upper end of container 16b is configured more narrowly than the lower end of container 16b, thereby forming a wedge shaped container. The material in side compartments 32b, 36b may have a wedge shape which is complementary to the resulting wedged shape of compartments 32b, 36b, thereby preventing the material from slipping out of the compartments. In one embodiment, the material in compartment 34b is maintained therein through the use of an adhesive.

It will be appreciated, however, that a wedged fit may also be accomplished in an embodiment in which the material is in a single piece and the container lacks compartmentalization by narrowing the upper end of the container with respect to the lower end. Optionally, the material is complimentary to the wedged shape of the container.

FIG. 4 demonstrates the use of compartments 32c, 34c, 36c and the placement of different pieces of supporting material 18c in upper portions of the compartments 32c, 34c, 36c only. Solution 24c permeates supporting material 18c and fills the lower portion of container 16c. Material pieces 18c may be maintained in a desired position within the compartments through the use of an adhesive, for example, or by lips 29c, 31c. Lid 28c fits frictionally on container 16c.

The frictional fit configuration of lid 28c is another example of a means for sealing the open end 26c of container 16c. Other examples of means for sealing the open end 26 of container 16 include a sealed pouch disposed about the entire containing device 14. In one embodiment, the sealed pouch is filled with disinfecting solution which surrounds containing device 14 and permeates supporting material 18. Such sealed pouches may be particularly useful with the embodiments shown in FIGS. 2 and 3 are not shown with lids.

In another embodiment, any of the above embodiments can also be utilized without a solution that contacts the instruments 12. Accordingly, instruments 12 are inserted into a dry supporting material 18. Such a configuration enables the instruments to be maintained in a clean condition and to be held in an upright position ready for use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of using an apparatus for holding, cleaning and maintaining aseptic condition of dental instruments such as endodontic files or the like which need to be repeatedly withdrawn and replaced while performing a procedure such as a root canal on a patient, and wherein the dental instruments have a handle portion and a distal working end portion, the apparatus including a container having an open end through which the instruments are inserted and withdrawn from the container, a cellular foam material disposed within said container, said cellular foam material comprising a support material that is (a) sufficiently porous and deformable to allow the distal working end of the instruments to be inserted into the support material without bending, blunting or damaging the distal working end, (b) sufficiently strong and rigid to both clean debris from the distal working end as it is inserted into the support material when being replaced into the container, as well as gripping the distal working end of the instruments when inserted into the support material so that the replaced instruments are held in an essentially upright, ready position for grasping the handle portion when removal is desired, and a disinfecting solution disposed and placed within the container so as to be in contact with the distal working end portion of the instruments after they are placed and are being held within the container, the method comprising the steps of:

withdrawing an instrument from the container by grasping a handle portion of the instrument and pulling the distal working end of the instrument from the cellular foam material;

performing a procedure with the instrument on the patient;

reinserting the distal working end of the instrument into the cellular foam material;

removing debris from the distal working end as it is inserted into the cellular foam material; and bringing the distal working tip of the instrument into contact with the disinfecting solution once it is replaced and held by the cellular foam material.

2. A method as defined in claim 1 wherein the support material is comprised of a cellular foam and wherein the cellular foam is permeated with the disinfecting solution, and wherein the step of bringing the distal working tip of the instrument into contact with the disinfecting solution occurs as the instrument is inserted into the support material and held in place thereby.

3. A method as defined in claim 1 wherein the support material is comprised of a cellular foam that extends partially into said container so as to form a space beneath the cellular foam for holding the disinfecting solution, and wherein the method of bringing the distal tip of the instrument into contact with the disinfecting solution comprises inserting at least a portion of the distal working tip through the cellular foam until said portion extends beyond the cellular tip and into the disinfecting solution.

4. A method as defined in claim 1 wherein the container further comprises a closeable lid for the container and the method further comprises the step of enclosing the instruments within the container by placing the lid over the opening of the container while one or more of the instruments are being held in the container to help maintain their aseptic condition.

5. A method as defined in claim 1 wherein the container is formed with separate compartments for each instrument, and wherein the method comprises the step of removing and replacing a given instrument from or into a single compartment.

6. A method as defined in claim 1 further comprising the steps of removing and replacing a handle portion of an instrument while it is being held by the support material.

7. An apparatus for holding dental instruments such as endodontic files or the like which need to be repeatedly withdrawn and replaced while performing a procedure such as a root canal on a patient, and wherein the dental instruments have a handle portion and a distal working end portion that needs to be cleaned and maintained in all aseptic condition both during use while repeatedly withdrawing and replacing the instruments during the procedure, as well as afterwards during storage of the instruments, the apparatus comprising:

a container having an open end through which the instruments are inserted and withdrawn from the container;

a cellular foam material disposed within said container and immediately adjacent said open end, said cellular foam material comprising a support material that is (a) sufficiently porous and deformable to allow the distal working end of the instruments to be repeatedly withdrawn and re-inserted into the support material without bending, blunting or damaging the distal working end, and (b) sufficiently strong and rigid to both clean debris from the distal working end as it is inserted into the support material when being replaced into the container, as well as gripping the distal working end of the instruments when inserted into the supporting material so that the replaced instruments are held in an essentially upright, ready position for grasping or attachment of the handle portion when removal is desired; and a disinfecting solution disposed and placed within the container so as to be contained beneath the support material or so as to permeate the support material in order to be in contact with the distal working end portion of the instruments after they are placed and are being held within the container.

8. An apparatus as defined in claim 7 wherein the support material is permeated with the disinfecting solution.

9. An apparatus as defined in claims 7 or 8 wherein the support material extends partially into said container so as to form a space beneath the support material for holding the disinfecting solution, and wherein the disinfecting solution is held within said space.

10. An apparatus as defined in claim 9 wherein the support material is comprised of a cellular foam.

11. An apparatus as defined in claim 9 wherein the disinfecting solution comprises an antimicrobial agent.

12. An apparatus as defined in claim 9 wherein the support material is a synthetic material.

13. An apparatus as defined in claim 9 wherein the container comprises means for retaining the support material in a desired position within the container.

14. An apparatus as defined in claim 13 wherein the means for retaining the support material in a desired position comprises a lip formed about said opening of the container.

15. An apparatus as defined in claim 13 wherein the means for retaining the support material in a desired position comprises an adhesive material placed around said opening of the container.

16. An apparatus as defined in claim 13 wherein said container has a larger bottom than said opening and wherein said support material has a corresponding size and shapes and wherein said means for retaining the support material in a desired position is provided by a wedged fit between the support material and the container.

17. As apparatus as defined in claim 9 wherein said container is formed with a plurality of individual compartments for separately holding individual instruments, and wherein said support material is separately placed into each compartment.

18. An apparatus as defined in claim 17 further comprising means for sealing the open end of said container to permit selective opening and closure thereof.

19. An apparatus as defined in claim 18 wherein said means for scaling the open end comprises a lid attached by a hinge to said container.

20. An apparatus as defined in claim 18 wherein said means for sealing the open end comprises a lid which as attachable to the open end of the container by a friction fit.

* * * * *

UNITED STATES PATENT AND TRADEMARK OFFICE
CERTIFICATE OF CORRECTION

PATENT NO. : 5,967,778
DATED : Oct. 19, 1999
INVENTOR(S) : Franceso Riitano

It is certified that error appears in the above-identified patent and that said Letters Patent is hereby corrected as shown below:

Col. 3, line 21, after "repeatedly" delete "to"

Col. 3, line 26, after "is" insert --to--

Col. 3, line 30, after "invention" delete "is"

Col. 7, line 10, after "which" change "permit" to --permits--

Col. 7, line 47, change "location" to --locations--

Col. 11, line 61, after "as" change "cndodontic" to --endodontic--

Col. 12, line 67, after "in" change "all" to --an--

Col. 14, line 18, after "and" change "shapes" to --shape--

Signed and Sealed this

Thirteenth Day of February, 2001

Attest:

NICHOLAS P. GODICI

*Attesting Officer*    *Acting Director of the United States Patent and Trademark Office*